United States Patent
Nakamura

(10) Patent No.: US 8,865,942 B2
(45) Date of Patent: Oct. 21, 2014

(54) 2-CYANOPHENYLBORONIC ACID OR ESTER THEREOF IN WHICH IMPURITIES ARE DECREASED, AND PRODUCTION METHOD THEREOF

(75) Inventor: Shinichiro Nakamura, Shunan (JP)

(73) Assignee: Tosoh Finechem Corporation, Yamaguchi (JP)

( * ) Notice: Subject to any disclaimer, the term of this patent is extended or adjusted under 35 U.S.C. 154(b) by 1047 days.

(21) Appl. No.: 12/226,747

(22) PCT Filed: Apr. 11, 2007

(86) PCT No.: PCT/JP2007/057945
§ 371 (c)(1),
(2), (4) Date: Oct. 27, 2008

(87) PCT Pub. No.: WO2007/125750
PCT Pub. Date: Nov. 8, 2007

(65) Prior Publication Data
US 2009/0184289 A1    Jul. 23, 2009

(30) Foreign Application Priority Data
Apr. 28, 2006 (JP) ................................. 2006-124947

(51) Int. Cl.
*C07F 5/02* (2006.01)

(52) U.S. Cl.
CPC ...................................... *C07F 5/025* (2013.01)
USPC .......................................................... 568/1

(58) Field of Classification Search
USPC ............. 252/182.12; 526/131, 128, 129, 160, 526/170, 172, 348; 502/152; 568/1
See application file for complete search history.

(56) References Cited

U.S. PATENT DOCUMENTS

| | | | |
|---|---|---|---|
| 5,849,912 A | | 12/1998 | Akasaka et al. |
| 6,211,311 B1 * | | 4/2001 | Wang et al. .................... 526/131 |
| 6,525,099 B1 * | | 2/2003 | Arnold et al. ................. 514/605 |
| 2004/0254076 A1 * | | 12/2004 | Nishida et al. ................ 504/193 |

FOREIGN PATENT DOCUMENTS

| | | |
|---|---|---|
| DE | 101 50 610 | 4/2003 |
| EP | 0 675 118 | 10/1995 |
| JP | 08-231507 | 9/1996 |
| WO | 03/033505 | 4/2003 |

OTHER PUBLICATIONS

Jesper Kristensen, 2001,Organic Letters, vol. 3, 1435-1437.*
Jesper Kristensen et al. "*Synthesis of Ortho Substituted Arylboronic Esters by in Situ Trapping of Unstable Lithio Intermediates*", Organic Letters, vol. 3, No. 10, pp. 1435-1437 (2001).
Andrew P. Thomas et al. "*The Synthesis and Biological Activity of Tetrahydroquinoline Angiotensin II Antagonists Containing A Substituted Biphenyltetrazole Group*", Bioorganic & Medicinal Chemistry Letters, vol. 4, No. 21, pp. 2615-2620 (1994).

* cited by examiner

*Primary Examiner* — Monique Peets
(74) *Attorney, Agent, or Firm* — Wenderoth, Lind & Ponack, LLP.

(57) ABSTRACT

A method for producing high-purity 2-cyanophenylboronic acid, characterized by reacting benzonitrile, lithium 2,2,6,6-tetramethylpiperidide, and trialkoxyborane, adding an aqueous acidic solution to a reaction solution containing the obtained 2-cyanophenylboronic acid, carrying out a contact treatment at a pH of below 7 in the presence of a water-immiscible organic solvent, and then obtaining the 2-cyanophenylboronic acid from the organic layer.

7 Claims, No Drawings

2-CYANOPHENYLBORONIC ACID OR ESTER THEREOF IN WHICH IMPURITIES ARE DECREASED, AND PRODUCTION METHOD THEREOF

TECHNICAL FIELD

The present invention relates to high-purity 2-cyanophenylboronic acid or an ester thereof, which can become a raw material of a medicine and an electronic material, and a production method thereof.

BACKGROUND ART

2-Cyanophenylboronic acid and its derivatives are effective as a raw material of a medicine and an electronic material such as liquid crystals used in the Suzuki coupling reaction.

Examples of common boronic acid production methods include: carrying out a transmetallation reaction between an aryl silane or an aryl stannane compound with boron tribromide, and then hydrolyzing the resulting product; coupling a halogenated aryl or an aryl triflate with pinacol borane or bispinacol diborate using a transition metal catalyst; and converting a halogenated aryl to an organic metal compound such as an aryl magnesium halide and aryl lithium, then reacting with trialkylborate.

While the latter method is commonly used as a method for producing industrially, even among boronic acids, since organic magnesium compounds react with a nitrile group, a method in which n-butyllithium and a halogenated benzonitrile are reacted at a low temperature is commonly used for cyanophenylboronic acids. In particular, 2-cyanophenylboronic acid can only be obtained at a low yield even if n-butyllithium is used. Patent Document 1 describes a method in which a subject compound is obtained in a good yield by reacting 2-bromobenzonitrile with a tertiary butyl lithium.

However, there are problems with this method, such as the fact that the raw materials, 2-bromobenzonitrile and tertiary butyl lithium, are expensive, and the fact that purity does not improve because byproducts which are difficult to separate, such as 2-cyano-3-bromophenylboronic acid, are produced. Another exemplary method is to obtain a pinacol ester of the subject cyanophenylboronic acid by coupling a halogenated benzonitrile with pinacol borane or bispinacol diborate using a noble metal catalyst. However, there are problems with this method as an industrial production method, in that the halogenated benzonitrile as a raw material and the pinacol borane raw material are expensive, and that an expensive catalyst is required for the coupling.

Non-patent Document 1 reports that a neopentyl glycol ester of 2-cyanophenylboronic acid can be obtained via an ortholithiation reaction by lithium 2,2,6,6-tetramethylpiperidide with benzonitrile as a raw material, then esterifying the resulting product with neopentyl glycol, and solidifying the resulting organic phase. However, in this method, the obtained neopentyl glycol ester of 2-cyanophenylboronic acid is mixed in a 3.5:1 proportion with N-benzoyl-2,2,6,6-tetramethylpiperidine. This method has the problem that, even though purification by recrystallization with a heptane solvent is carried out, once N-benzoyl-2,2,6,6-tetramethylpiperidine is introduced in the crystallization of the 2-cyanophenylboronic acid or in the subsequent esterification step, separation of the N-benzoyl-2,2,6,6-tetramethylpiperidine is difficult, so that the purity of the 2-cyanophenylboronic acid and its derivatives does not improve.

[Patent Document 1] European Patent EP-0675118A specification

[Non-patent Document 1] Organic Lett., 3(10), 1435 to 1437 (2001)

DISCLOSURE OF THE INVENTION

Problem to be Solved by the Invention

The problem to be solved by the present invention is to provide a high-purity 2-cyanophenylboronic acid or an ester thereof, and a method for synthesizing 2-cyanophenylboronic acid or an ester thereof in a high purity.

Means for Solving the Problems

As a result of intensive investigations into solving the above-described problems, the present inventor discovered that when a reaction solution of 2-cyanophenylboronic acid synthesized by reacting benzonitrile, lithium 2,2,6,6-tetramethylpiperidide, and trialkoxyborane is treated with an aqueous acidic solution, by making the pH of the aqueous phase to be below 7, hydrolysis to N-benzoyl-2,2,6,6-tetramethylpiperidine does not occur even in a system in which water is present, meaning that 1-phenyl-1-(2,2,6,6-tetramethylpiperidin-1-yl)methyl imine is stably present. The present inventor further discovered that by subsequently extracting with an organic solvent, 1-phenyl-1-(2,2,6,6-tetramethylpiperidin-1-yl)methyl imine can be stably and selectively extracted to an acidic aqueous phase, and as a result 2-cyanophenylboronic acid and its derivatives can be obtained having a high chemical purity, thereby completing the present invention.

Specifically, the present invention relates to 2-cyanophenylboronic acid and an ester thereof which is defined by the following inventive features and which has a chemical purity of 98% or more, and a production method thereof.

(1) 2-Cyanophenylboronic acid or a 2-cyanophenylboronate, characterized in that a content of 1-phenyl-1-(2,2,6,6-tetramethylpiperidin-1-yl)methyl imine is 0.001 mol % or more and 0.5 mol % or less.

(2) The 2-cyanophenylboronate according to (1), wherein the 2-cyanophenylboronate is a 1,3-propanediol ester of 2-cyanophenylboronic acid.

(3) A method for producing high-purity 2-cyanophenylboronic acid, characterized by reacting benzonitrile, lithium 2,2,6,6-tetramethylpiperidide, and trialkoxyborane, adding an aqueous acidic solution to a reaction solution containing the obtained 2-cyanophenylboronic acid, carrying out a contact treatment at a pH of below 7 in the presence of a water-immiscible organic solvent, and then obtaining the 2-cyanophenylboronic acid from the organic layer.

(4) A method for producing a high-purity a 2-cyanophenylboronate, characterized by reacting benzonitrile, lithium 2,2,6,6-tetramethylpiperidide, and trialkoxyborane, adding an aqueous acidic solution to a reaction solution containing the obtained 2-cyanophenylboronic acid, carrying out a contact treatment at a pH of below 7 in the presence of a water-immiscible organic solvent, and then esterifying the 2-cyanophenylboronic acid contained in the organic layer.

(5) The production method according to (3) or (4), characterized in that the trialkoxyborane is triisopropoxyborane.

(6) The production method according to any of (2) to (5), characterized in that the aqueous acidic solution used in the contact treatment is hydrochloric acid and/or sulfuric acid.

(7) The production method according to (4), wherein the 2-cyanophenylboronate is a 1,3-propanediol ester of 2-cyanophenylboronic acid.

Effects of the Invention

According to the method of the present invention, high-purity 2-cyanophenylboronic acid or an ester thereof can be efficiently obtained.

The 2-cyanophenylboronic acid or ester thereof obtained by the method of the present invention is high-purity 2-cyanophenylboronic acid or an ester thereof in which the content of 1-phenyl-1-(2,2,6,6-tetramethylpiperidin-1-yl)methyl imine is 0.001 mol % or more and 0.5 mol % or less.

BEST MODE FOR CARRYING OUT THE INVENTION

The present invention will now be described in more detail.

The present invention relates to high-purity 2-cyanophenylboronic acid or an ester thereof. Examples of such an ester include chain dialkyl esters, such as dimethylester, diethyl ester, and diisopropyl ester, and cyclic esters with a diol, such as ethylene glycol ester, 1,3-propanediol ester, neopentyl glycol ester, a catechol ester, and a pinacol ester. These esters can be produced by a commonly-used esterification method, such as by optionally isolating the 2-cyanophenylboronic acid, and then carrying out a typical esterification in a state in which the 2-cyanophenylboronic acid is dissolved in a water-immiscible organic solvent.

High-purity 2-cyanophenylboronic acid or an ester thereof can be produced from benzonitrile by a method using lithium 2,2,6,6-tetramethylpiperidide and trialkoxyborane.

Production of high-purity 2-cyanophenylboronic acid can be achieved by reacting benzonitrile, lithium 2,2,6,6-tetramethylpiperidide, and trialkoxyborane, bringing the resulting solution into contact with an aqueous acidic solution, and maintaining the pH of the aqueous phase at that stage to below 7. The impurity N-benzoyl-2,2,6,6-tetramethylpiperidine, which is disclosed in the Supporting Information of the above Non-patent Document 1, is thought to be produced by generating the 1-phenyl-1-(2,2,6,6-tetramethylpiperidin-1-yl)methylimine by the addition of lithium 2,2,6,6-tetramethylpiperidide to the nitrile group of the benzonitrile, and subsequently changing it into N-benzoyl-2,2,6,6-tetramethylpiperidine by undergoing hydrolysis under alkaline conditions during the hydrolysis with saturated ammonium chloride water.

This intermediate 1-phenyl-1-(2,2,6,6-tetramethylpiperidin-1-yl)methyl imine is stably present under acidic conditions of a pH of less than 7 without undergoing a hydrolysis reaction. While 2-cyanophenylboronic acid is selectively extracted in the organic phase, 1-phenyl-1-(2,2,6,6-tetramethylpiperidin-1-yl)methyl imine is extracted in the aqueous acidic solution. This is characteristic in the production of 2-cyanophenylboronic acid using lithium 2,2,6,6-tetramethylpiperidide. For example, in cases where a lithium amide other than lithium 2,2,6,6-tetramethylpiperidide, such as lithium diisopropyl amide or lithium 2,6-dimethylpiperide, is used, not only is 2-cyanophenylboronic acid not formed, but nucleophilic addition onto the nitrile group of the amide selectively proceeds, so that N,N-substituted benzamide is quantitatively formed via a benzamidine derivative.

When such a lithium amide other than lithium 2,2,6,6-tetramethylpiperidide is used, even if the reaction solution is hydrolyzed with an aqueous acidic solution after the reaction, the intermediate benzamidine derivative is not stably present, and is easily hydrolyzed to a benzamide compound, which is selectively extracted to the organic phase side. It is clear, from the fact where the partitioning behavior into an aqueous phase, and the lack of carbonyl-specific absorbance which should be found near 1650 cm$^{-1}$ by the infrared spectrometry in the following examples, that the 1-phenyl-1-(2,2,6,6-tetramethylpiperidin-1-yl)methyl imine is not hydrolyzed as far as N-benzoyl-2,2,6,6-tetramethylpiperidine, namely, that the N-benzoyl-2,2,6,6-tetramethylpiperidine described in the above documents is not present.

As the trialkoxyborane, trimethoxyborane, triethoxyborane, triisopropoxyborane, and tributoxyborane which are commonly used in boronic acid synthesis may be used. Preferred examples include trimethoxyborane and triisopropoxyborane. An especially preferred example is triisopropoxyborane.

The method for synthesizing lithium 2,2,6,6-tetramethylpiperidide is not especially limited. One example of such a method is to add a solution of n-butyllithium in hexane to a solution of 2,2,6,6-tetramethylpiperidine in THF to lithiate the 2,2,6,6-tetramethylpiperidine. The prepared lithium 2,2,6,6-tetramethylpiperidide does not have to be completely dissolved in the solution. A slurry containing crystals of lithium 2,2,6,6-tetramethylpiperidide may also be used in the reaction.

When preparing the lithium 2,2,6,6-tetramethylpiperidide from 2,2,6,6-tetramethylpiperidine and n-butyllithium, the n-butyllithium may be used in a mole ratio of 0.8 or more and 1.05 or less with respect to the 2,2,6,6-tetramethylpiperidine. If the n-butyllithium is more than the 2,2,6,6-tetramethylpiperidine, the n-butyllithium itself reacts with the benzonitrile, so that a valerophenone is formed as a byproduct, which is not preferable. Accordingly, it is preferred to use the 2,2,6,6-tetramethylpiperidine slightly in excess.

The lithium 2,2,6,6-tetramethylpiperidide may be used in a mole ratio in the range of from 0.9 to 2 with respect to the raw material benzonitrile.

The trialkoxyborane may be used in a mole ratio in the range of from 0.9 to 5 with respect to the benzonitrile.

The addition order of the substrates when synthesizing 2-cyanophenylboronic acid is not especially limited. However, considering the thermal stability of the ortholithio form of the lithium 2,2,6,6-tetramethylpiperidide and benzonitrile, it is preferred to add the trialkoxyborane and benzonitrile to the prepared lithium 2,2,6,6-tetramethylpiperidide solution successively or simultaneously.

The solvent used in the reaction is not especially limited, as long as it does not affect the subject reaction. The reaction can even be carried out without a solvent, or using a solvent such as an aliphatic hydrocarbon like hexane and heptane, an aromatic hydrocarbon like toluene, and an ether like diethyl ether and THF. An especially preferred example is THF.

The reaction temperature for the synthesis of the 2-cyanophenylboronic acid may be in the range of from −100° C. to 0° C. If the temperature is lower than −100° C., the reaction rate is slow, which is not preferable. If the temperature is higher than 0° C., byproduct reactions increase, which is not preferable. Especially preferred temperature is −80° C. to −20° C.

The aqueous acidic solution addition treatment is usually carried out at a temperature of −20 to 50° C., and 0 to 20° C. is especially preferred. At this temperature, the aqueous acidic solution may be added to the reaction solution, or the reaction solution may be added to the aqueous acidic solution in a short period of time. However, since the hydrolysis from 1-phenyl-1-(2,2,6,6-tetramethylpiperidin-1-yl)methyl imine to N-benzoyl-2,2,6,6-tetramethylpiperidine rapidly proceeds at the alkali side, a preferred production method is to add the reaction solution to the aqueous acidic solution. The acid amount used in the aqueous acidic solution addition treatment may be an amount capable of making the pH of the aqueous phase during extraction to be below 7. Examples of the acid which can be used for hydrolysis include an aqueous solution of a mineral acid such as hydrochloric acid, sulfuric acid, phosphoric acid, and nitric acid. Preferred examples include hydrochloric acid and sulfuric acid.

The separation of the 2-cyanophenylboronic acid and the 1-phenyl-1-(2,2,6,6-tetramethylpiperidin-1-yl)methyl imine can be carried out even more efficiently by having water and organic solvents forming two layers present in the solution which has undergone the aqueous acidic solution contact treatment. As long as it does not adversely affect the synthesis reaction of the 2-cyanophenylboronic acid, these water-immiscible organic solvents can be added prior to the reaction. Organic solvents which might react with the lithium 2,2,6,6-tetramethylpiperidide or the like may be added at any stage up until the separation step of the post-reaction synthesized aqueous acidic solution and the post-contact-treatment aqueous phase. Examples of water-immiscible organic solvents which can be used include esters of carbonic acids such as ethyl acetate and propyl acetate, ethers such as diethyl ether and diisopropyl ether, halogenated hydrocarbons such as dichloromethane and chloroform, aromatic hydrocarbons such as toluene and xylene, and aliphatic hydrocarbons such as hexane and heptane. From the standpoint of extraction efficiency, an especially preferred example is ethyl acetate.

To reduce the mixed amount of 1-phenyl-1-(2,2,6,6-tetramethylpiperidin-1-yl)methyl imine in the 2-cyanophenylboronic acid or ester thereof, after the aqueous acidic solution addition treatment, the resulting 2-cyanophenylboronic acid organic phase may optionally be further washed with water or an aqueous acidic solution. By repeating this acid washing, the mixed amount of 1-phenyl-1-(2,2,6,6-tetramethylpiperidin-1-yl)methyl imine can be markedly reduced. However, since the yield decreases due to part of the 2-cyanophenylboronic acid also being extracted in the aqueous acidic solution, it is not effective to carry out the washing more than is necessary. It is preferred to carry out the washing 1 to 3 times so that the following coupling step is not affected, thereby forming a composition having a 1-phenyl-1-(2,2,6,6-tetramethylpiperidin-1-yl)methyl imine content of 0.001 mol % or more and 0.5 mol % or less with respect to the 2-cyanophenylboronic acid. Furthermore, as a result of the above operation, the resulting 2-cyanophenylboronic acid can have a chemical purity of 98% or more.

EXAMPLES

Effects of the present invention will now be illustrated by the following examples. However, the present invention is not limited to these examples.
Analysis Conditions
Liquid Chromatography Analysis
Test solution: A sample was dissolved in a mixed solution in which water/acetonitrile was 40:60 (V/V) so that the concentration of the 2-cyanophenylboronic acid was 1 mg/1 ml or less.
Apparatus: Tosoh High-pressure Gradient System (manufactured by Tosoh Corporation)
Detector: UV-8020 (manufactured by Tosoh Corporation)
Column: YMC A-302 (4.6 mm φ×150 mL)
Temperature: 35° C.
Mobile Phase:
A solution: Water/acetonitrile/70% perchloric acid (900/100/1 V/V/V)
B solution: Water/acetonitrile/70% perchloric acid (100/900/1 V/V/V)

Gradient Method: B solution 30%→(3 min)→30% (12 min)→100%→(5 min)→100%
Flow amount: 0.7 ml/min
Detection Wavelength: UV 267 nm
Injection Amount: 5 µl

Example 1

Synthesis Example of 2-Cyanophenylboronic Acid

In a 300 ml nitrogen-substituted flask, 21.6 g (0.153 mol) of 2,2,6,6-tetramethylpiperidine was dissolved in 130 ml of THF. Then, to the resulting solution, 96 ml (0.153 mol) of a 15% solution of n-butyllithium in hexane was added dropwise at −10° C. to prepare lithium 2,2,6,6-tetramethylpiperidide. This solution was cooled to −78° C., and then 67 ml (0.291 mol) of triisopropoxyborane was added dropwise thereto. Next, 15 g (0.146 mol) of benzonitrile was added dropwise, and then the resulting solution was aged for 2 hours at the same temperature. The temperature of the reaction solution was increased to room temperature, and then the solution was hydrolyzed by 225 ml of 2N HCl. The solution was charged with 150 ml of ethyl acetate and stirred, and then the acid phase (pH<1) was separated. The aqueous phase was extracted with 105 ml of ethyl acetate. Then, the two organic phases were mixed and washed with 90 ml of saturated brine. The resulting organic phase was then dried with anhydrous magnesium sulfate and concentrated using an evaporator. The concentrated solution was charged with 100 ml of dichloromethane, and then the solution was charged with 50 ml of hexane at 0° C. The precipitated crystals were filtered and dried to obtain 7.3 g of 2-cyanophenylboronic acid crystals. The purity of the 2-cyanophenylboronic acid was 98.7%, in which 0.3 mol % of 1-phenyl-1-(2,2,6,6-tetramethylpiperidin-1-yl)methyl imine was included.

Example 2

In a 3 L nitrogen-substituted flask, 264 g (1.87 mol) of 2,2,6,6-tetramethylpiperidine was dissolved in 535 ml of THF. Then, to the resulting solution, 1,150 ml (1.87 mol) of a 15% solution of a solution of n-butyllithium in hexane was added dropwise at −10° C. to prepare lithium 2,2,6,6-tetramethylpiperidide. This solution was cooled to −50° C., and then a mixed solution of 492 ml (2.13 mol) of triisopropoxyborane and 177 ml (1.73 mol) of benzonitrile was added dropwise thereto. The resulting solution was aged for 2 hours at the same temperature. It was confirmed that the conversion rate of the benzonitrile was 96%, and the reaction yield of the 2-cyanophenylboronic acid was 71.5%, with 15.4 mol % of 1-phenyl-1-(2,2,6,6-tetramethylpiperidin-1-yl)methyl imine as a byproduct. This reaction solution was charged into 1,540 ml of a 3N HCl solution to carry out hydrolysis. After carrying out a two-layer separation, the acid phase (pH=1) was washed 3 times with 715 ml of ethyl acetate. The mixed solution of these organic phases contained, based on the charged benzonitrile, 61.5 mol % of 2CPBA and 7.5 mol % of 1-phenyl-1-(2,2,6,6-tetramethylpiperidin-1-yl)methyl imine. This organic phase was washed with 14 ml of 0.2 N HCl, and then washed twice with 100 ml of water and 714 ml of saturated brine to obtain 2.94 kg of an organic phase in which 2-cyanophenylboronic acid was dissolved. This solution contained 146 g of 2-cyanophenylboronic acid and 0.4 mol % of 1-phenyl-1-(2,2,6,6-tetramethylpiperidin-1-yl)methyl imine with respect to the 2-cyanophenylboronic acid.

Example 3

The organic phase obtained in Example 2 was charged with 77 ml of 1,3-propanediol, and the resulting solution was stirred at room temperature for 2 hours. The free aqueous layer was separated, and then the solvent was removed by distillation using an evaporator. The residual oily substance was dissolved in 700 ml of dichloromethane, and the resulting solution was washed with 153 ml of water. The obtained organic phase was then dried with anhydrous magnesium sulfate, and turned into a solid by drying under reduced pressure using an evaporator. While stirring with a magnetic stirrer, 450 ml of hexane was slowly added dropwise to the oily residue under ice cooling to cause crystals to precipitate. The obtained crystals were washed with 500 of chilled hexane, and dried for 12 hours under reduced pressure at room temperature to obtain 184 g of the 1,3-propanediol ester of 2-cyanophenylboronic acid (2-(1,3,2-dioxaborinan-2-yl)benzonitrile). The purity was 99.4%, and these crystals contained 0.45 mol % of 1-phenyl-1-(2,2,6,6-tetramethylpiperidin-1-yl)methyl imine.

Example 4

In a 300 ml nitrogen-substituted flask, 11.6 g (0.082 mol) of 2,2,6,6-tetramethylpiperidine was dissolved in 63 ml of THF. Then, to the resulting solution, 53 ml (0.082 mol) of a 15% solution of n-butyllithium in hexane was added dropwise at −20° C. to prepare lithium 2,2,6,6-tetramethylpiperidide. This solution was cooled to −80° C., and then 22 ml (0.933 mol) of triisopropoxyborane was added thereto. Then, 8 ml (0.0756 mol) of benzonitrile was added dropwise, and the resulting solution was aged for 15 minutes at the same temperature. The temperature of the solution was then increased to −40° C. This reaction solution was charged into 69 ml of a 3N HCl solution, and the resulting solution was then charged with 73 ml of dichlorormethane to carry out a two-layer separation. The organic phase was washed twice with 73 ml of saturated brine, and then dried with anhydrous magnesium sulfate. The organic phase was concentrated under reduced pressure, and then the concentrated solution was dissolved in 40 ml of dichloromethane. The resulting solution was charged with 4 ml (0.056 mol) of 1,3-propanediol, and then stirred for 2 hours at room temperature. The reaction solution was dried with anhydrous magnesium sulfate, and then concentrated and dried using an evaporator. The concentrated solution was charged with 10 ml of toluene at room temperature. The precipitated crystals were filtered, washed with hexane, and then dried overnight at room temperature under reduced pressure to obtain 1.6 g of white crystals. From the following analysis results, this compound was identified as being 1-phenyl-1-(2,2,6,6-tetramethylpiperidin-1-yl)methyl imine. $^1$H-NMR (300 MHz, CDCl$_3$) 9.1 (b, 2H), 7.66 (m, 1H), 7.61 to 7.57 (m, 2H), 7.52 to 7.45 (m, 2H), 1.92 (m, 6H), 1.52 (s, 12H) LC-MS (m/z=245)

No carbonyl absorption in IR (KBr) 1650 to 1700 cm$^{-1}$.

6.93 g of white crystals was obtained by charging 50 ml of heptane into the filtrate and cooling with ice. These crystals were a propanediol ester of 2-cyanophenylboronic acid containing 8.4% of 1-phenyl-1-(2,2,6,6-tetramethylpiperidin-1-yl)methyl imine.

Example 5

In a 300 ml nitrogen-substituted flask, 21.6 g (0.153 mol) of 2,2,6,6-tetramethylpiperidine was dissolved in 130 ml of THF. Then, to the resulting solution, 96 ml (0.153 mol) of a 15% solution of n-butyllithium in hexane was added dropwise at −10° C. to prepare lithium 2,2,6,6-tetramethylpiperidide. This solution was cooled to −78° C., and then 67 ml (0.291 mol) of triisopropoxyborane was added dropwise thereto. Next, 15 g (0.146 mol) of benzonitrile was added dropwise, and then the resulting solution was aged for 2 hours at the same temperature. The temperature of the reaction solution was increased to room temperature, and then the solution was hydrolyzed by 230 ml of 2N H$_2$SO$_4$. The solution was charged with 150 ml of ethyl acetate and stirred, and then the acid phase (pH<1) was separated. The aqueous phase was extracted with 100 ml of ethyl acetate. Then, the two organic phases were mixed and washed with 90 ml of saturated brine. The resulting organic phase was then dried with anhydrous magnesium sulfate and concentrated using an evaporator. The concentrated solution was charged with 100 ml of dichloromethane, and then the solution was charged with 50 ml of hexane at 0° C. The precipitated crystals were filtered and dried to obtain 6.8 g of 2-cyanophenylboronic acid crystals. The purity of the 2-cyanophenylboronic acid was 98.5%, in which 0.4 mol % of 1-phenyl-1-(2,2,6,6-tetramethylpiperidin-1-yl)methyl imine was included.

Comparative Example

Method Disclosed in Document 2-(1,3,2-dioxaborinan-2-yl)benzonitrile was synthesized according to the method described in the above-described Non-patent Document 1, except that 1,3-propanediol was used instead of neopentanediol.

In a 300 ml nitrogen-substituted flask, 10.6 g (0.075 mol) of 2,2,6,6-tetramethylpiperidine was dissolved in 80 ml of THF. Then, to the resulting solution, 48 ml (0.075 mol) of a 15% solution of n-butyllithium in hexane was added dropwise at −10° C. to prepare lithium 2,2,6,6-tetramethylpiperidide. This solution was cooled to −78° C., and then 23 ml (0.097 mol) of triisopropoxyborane was added thereto. Then, 5 ml (0.050 mol) of benzonitrile was added dropwise. The resulting solution was aged for 2 hours at the same temperature, and then the temperature of the solution was increased to room temperature. This reaction solution was charged with 200 ml of an aqueous saturated ammonium chloride solution, and then extracted three times with 200 ml of ethyl acetate. The organic phases were all mixed together, and then the resulting solution was dried with an hydrous sodium sulfate. The solvent was then removed by distillation under reduced pressure. The crude product was dissolved in 200 ml of toluene. The resulting solution was charged with 4.5 g (0.059 mol) of 1,3-propanediol, and then left overnight under stirring at room temperature. The toluene phase was extracted three times with 100 ml of water. The obtained aqueous phases were mixed, and then the resulting aqueous phase was extracted three times with 100 ml of dichloromethane. The obtained dichloromethane phases were washed once with 100 ml of water. The toluene phases and the dichloromethane phases were all mixed together. The mixed organic phases were dried with anhydrous sodium sulfate, and then concentrated and dried under reduced pressure to obtain 11.10 g of crystals.

These crystals were mixed with 100 ml of heptane, and then the resulting solution was stirred under reflux for 1 hour. However, the crystals did not completely dissolve, and were in a slurry-like state. This slurry was cooled to room temperature, and then dried by filtration to obtain 4.5 g of crystals. The purity of the obtained 2-(1,3,2-dioxaborinan-2-yl)benzonitrile crystals was 67.7%, in which 21.4 mol % of N-benzoyl-2,2,6,6-tetramethylpiperidide was included. From IR measurement (KBr method) of the crystals, carbonyl absorbance near 1680 cm$^{-1}$ was confirmed.

INDUSTRIAL APPLICABILITY

According to the present invention, high-purity 2-cyanophenylboronic acid or an ester thereof can be obtained, which is useful as a raw material of a medicine and an electronic material.

The invention claimed is:

1. A method for producing high-purity 2-cyanophenylboronic acid, said method comprising: reacting benzonitrile, lithium 2,2,6,6-tetramethylpiperidide, and trialkoxyborane to obtain 2-cyanophenylboronic acid, adding a reaction solution containing the obtained 2-cyanophenylboronic acid to an aqueous acidic solution, carrying out a contact treatment at a pH of below 7 in the presence of a water-immiscible organic solvent, and then obtaining the high-purity 2-cyanophenylboronic acid from the organic layer.

2. A method for producing high-purity 2-cyanophenylboronate, said method comprising: reacting benzonitrile, lithium 2,2,6,6-tetramethylpiperidide, and trialkoxyborane to obtain 2-cyanophenylboronic acid, adding a reaction solution containing the obtained 2-cyanophenylboronic acid to an aqueous acidic solution, carrying out a contact treatment at a pH of below 7 in the presence of a water-immiscible organic solvent, and then esterifying the 2-cyanophenylboronic acid contained in the organic layer to obtain the high-purity 2-cyanophenylboronate.

3. The production method according to claim 1 or 2, wherein the trialkoxyborane is triisopropoxyborane.

4. The production method according to claim 1 or 2, wherein the aqueous acidic solution used in the contact treatment is hydrochloric acid and/or sulfuric acid.

5. The production method according to claim 2, wherein the 2-cyanophenylboronate is a 1,3-propanediol ester of 2-cyanophenylboronic acid.

6. The production method according to claim 3, wherein the aqueous acidic solution used in the contact treatment is hydrochloric acid and/or sulfuric acid.

7. The production method according to claim 3, wherein the aqueous acidic solution used in the contact treatment is hydrochloric acid and/or sulfuric acid.

* * * * *